United States Patent [19]

Onoda et al.

[11] 4,061,673

[45] Dec. 6, 1977

[54] MANUFACTURE OF METHACRYLIC ACID

[75] Inventors: Takeru Onoda; Masayuki Otake, both of Yokohama, Japan

[73] Assignee: Mitsubishi Chemical Industries Ltd., Tokyo, Japan

[21] Appl. No.: 710,340

[22] Filed: July 30, 1976

[51] Int. Cl.$^2$ ............................................. C07C 51/24
[52] U.S. Cl. ................................................ 260/526 N
[58] Field of Search .................................... 260/526 N

[56] References Cited

U.S. PATENT DOCUMENTS

| | | | |
|---|---|---|---|
| 3,917,673 | 11/1975 | Watkins | 260/526 N |
| 3,948,959 | 4/1976 | Cavaterra et al. | 260/526 N |

FOREIGN PATENT DOCUMENTS

| | | | |
|---|---|---|---|
| 1,338,845 | 8/1963 | France | 260/526 N |
| 504,014 | 1/1975 | Japan | 260/526 N |
| 49-100027 | 9/1974 | Japan | 260/526 N |
| 504,017 | 1/1975 | Japan | 260/526 N |
| 504,016 | 1/1975 | Japan | 260/526 N |
| 1,124,797 | 8/1968 | United Kingdom | 260/526 N |

*Primary Examiner*—Vivian Garner
*Attorney, Agent, or Firm*—Lane, Aitken, Dunner & Ziems

[57] ABSTRACT

Methacrylic acid is manufactured by oxidative dehydrogenation of isobutyric acid in vapor phase in the presence of a supported catalyst containing a heteropolyacid and/or a reduced form of the heteropolyacid. A highly siliceous material having a high water absorbability is used as a carrier for the catalyst to improve the conversion rate and selectivity as well as the catalyst durability.

6 Claims, No Drawings

MANUFACTURE OF METHACRYLIC ACID

BACKGROUND OF THE INVENTION

This invention relates to the manufacture of methacrylic acid, and more particularly to improvements in the manufacture of methacrylic acid by oxidative dehydrogenation of isobutyric acid.

Japanese Patent Laid-Open Application No. 48-78120 discloses a catalyst suitable for use in the manufacture of methacrylic acid by oxidative dehydrogenation of isobutyric acid. The catalyst mainly consists of a molybdophosphoric acid in which molybdenum may be partly replaced by vanadium and/or tungsten, and/or a reduced form of the molybdophosphoric acid.

Heteropolyacids, such as molybdophosphoric acid are crystals having a large quantity of water of crystallization at room temperature. At higher temperatures, however, water of crystallization is gradually released. A fine powder is obtained when the temperature is elevated to approximately the reaction temperature of the above-described oxidative dehydrogenation of isobutyric acid. It is then desirable to support the heteropolyacid on a suitable carrier when the heteropolyacid is used as a catalyst component in the reaction in vapor phase at elevated temperatures.

The above-described Japanese Patent Application also discloses that among suitable carriers are alumina, silica, diatomaceous earth, silicon carbide, and titania.

The use of a carrier, however, is often disadvantageous, depending upon the kind or properties of the carrier. In some cases, the catalytic activity or the selectivity to methacrylic acid is considerably reduced. In another case, the heteropolyacid constituting an active component of the catalyst tends to peel off or separate from the carrier leaving only a small amount of the heteropolyacid to be carried.

The activity per unit quantity of a catalyst increases as the content of heteropolyacid (fraction of supported heteropolyacid in the catalyst) increases. A catalyst with higher content of heteropolyacid, and hence with higher catalytic activity is then commercially more advantageous because the required amount of the catalyst can be reduced and a smaller reactor can be used.

The inventors have investigated the above problem and have found that a highly siliceous material having a considerable water absorbability is effective as a carrier for heteropolyacid.

SUMMARY OF THE INVENTION

Therefore, an object of this invention is to provide a process for the manufacture of methacrylic acid at higher rates of conversion of isobutyric acid and higher selectivities to methacrylic acid by oxidative dehydrogenation of isobutyric acid.

Another object of this invention is to provide a durable catalyst for use in the manufacture of methacrylic acid from isobutyric acid.

The attainment of the above objects is made possible by the instant invention which is directed to a process for manufacturing methacrylic acid by oxidative dehydrogenation of isobutyric acid in vapor phase in the presence of a catalyst carrying a heteropolyacid having the general formula:

$$H_{3+x}Mo_{12-x-y}W_yV_xPO_{40}$$

wherein $x$ and $y$ are independently 0, 1, 2, or 3 and $x + y < 5$, and/or a reduced form of the heteropolyacid, wherein a carrier for the catalyst has a $SiO_2$ content of at least 70% and a water absorbability of at least 60%.

DESCRIPTION OF THE PREFERRED EMBODIMENTS

An active component of the catalyst which can be used in the process of this invention is a heteropolyacid having the general formula:

$$H_{3+x}Mo_{12-x-y}W_yV_xPO_{40}$$

wherein $x = 0, 1, 2,$ or $3$, $y = 0, 1, 2,$ or $3$, and $x + y < 5$, and/or a reduced form of the heteropolyacid. A particular salt, for example, an ammonium salt of the heteropolyacid which may be decomposed by heat treatment into the acid may also be used in the preparation of the catalyst. The heteropolyacid having the above formula is orange yellow under normal conditions. It has been found that the heteropolyacid turns dark blue after being subjected to oxidative dehydrogenation because the heteropolyacid is reduced under reaction conditions. In other words, a reduced form of teh heteropolyacid serves as an actual catalyst during the reaction.

According to this invention, the heteropolyacid is supported by a specific carrier. The carrier should have a $SiO_2$ content of at least 70% and a water absorbability of at least 60%. It is to be noted that the water absorbability is measured according to ASTM C-121 and defined by the following formula:

Water absorbability = absorbed water amount (g)/dry carrier weight (g) × 100%

A preferred carrier has a $SiO_2$ content of at least 80% and a water absorbability of at least 75%.

As the carrier having a $SiO_2$ content of at least 70%, use may be made of highly siliceous materials such as silica gel and diatomaceous earth. Ordinary silica gel and diatomaceous earth which may contain various impurities are used, while they may contain any additive agent to improve the mechanical strength and other physical properties. Generally, these carriers may contain varying amounts of impurities, but according to this invention, they should have a $SiO_2$ content of at least 70%. Sometimes the impurities are washed off in acids to attain higher $SiO_2$ content of the supporting materials.

The use of lower siliceous materials having a $SiO_2$ content of less than 70% or non-siliceous materials such as alumina and titania results in undesirably low conversion rates of isobutyric acid and/or selectivities to methacrylic acid. Further, a carrier having a water absorbability of less than 60% is not desirable because the heteropolyacid will easily peel off or separate from the carrier so that a catalyst with high content of the heteropolyacid cannot be obtained.

The catalyst according to this invention may be prepared in a conventional manner for preparing a supported or carrier-type catalyst. For example, a catalyst may preferably be prepared by immersing a carrier in an aqueous solution of an active ingredient. The immersed carrier is evaporated to dryness and further dried.

According to the process of this invention, isobutyric acid is subjected to oxidative dehydrogenation in vapor phase in the presence of the above prepared catalyst, producing methacrylic acid. Oxygen and isobutyric acid are fed to the reaction zone so that the molar ratio of oxygen to isobutyric acid may be in the range from 0.1 to 10, preferably in the range from 0.5 to 5.0. In this case, isobutyric acid and oxygen may preferably be diluted with a gas which is inert to the reaction, such as nitrogen, water vapor, or carbon dioxide. Generally, isobutyric acid may be fed at a concentration of 0.1 to 10 vol% in a total gas charge.

The space velocity may adequately be selected within the range from 100 to 20,000 hr$^{-1}$, preferably within the range from 300 to 8,000 hr$^{-1}$. The reaction temperature may be generally 200° to 450° C, preferably 220° to 380° C. The reaction pressure is not critical in the process of this invention, while the reaction may be carried out normally at a pressure of 0.5 to 30 kg/cm$^2$, preferably 0.5 to 15 kg/cm$^2$ in absolute.

The following examples are illustrative of the invention and are not to be regarded as limitative.

A. PREPARATION OF CATALYSTS

Catalysts 1 and 2

Diatomaceous earth having a SiO$_2$ content of 89% was formed in a suitable pellet and then calcined at 700° C to obtain a pelleted product of diatomaceous earth which had a specific surface area of 20 m$^2$/g and a water absorbability of about 100%. The product was pulverized and then sieved to obtain a 24–40 mesh(Tyler) fraction.

In a solution of 2.0 g of 10-molybdo-2-vanadophosphoric acid (H$_5$Mo$_{10}$V$_2$PO$_{40}$) in 2.0 ml of water was immersed 2.0 g of the above pulverized diatomaceous earth. The immersed or active ingredient carrying diatomaceous earth was then dried at 100° C, obtaining Catalyst 1 with a content of the heteropolyacid of 50%.

Catalyst 2 with a content of the heteropolyacid of 20% was also prepared by following the above procedure in a similar manner.

Catalysts 3 and 4

Diatomaceous earth having a SiO$_2$ content of 89% was formed into a suitable pellet and then calcined at 1,000° C to obtain a formed product of diatomaceous earth having a specific surface area of 5 m$^2$/g and a water absorbability of 90%. The product was pulverized and then sieved to obtain a 24–40 mesh fraction, which was used as a carrier. According to the procedure described in the preparation of Catalyst 1, Catalysts 3 and 4 were prepared, which had contents of 10-molybdo-2-vanadophosphoric acid of 50% and 20%, respectively.

Catalysts 5 and 6

Silica gel having a specific surface area of 370 m$^2$/g, a water absorbability of 100%, and a particle size within the range of 24–40 mesh (manufactured and sold by Davison Co.) was used as a carrier. According to the procedure described in the preparation of Catalyst 1, Catalysts 5 and 6 were prepared, which had contents of 10-molybdo-2-vanadophosphoric acid of 50% and 20%, respectively.

Catalyst 7

The procedure described in the preparation of Catalyst 1 was repeated except that 9-molybdo-3-vanadophosphoric acid (H$_6$Mo$_9$V$_3$PO$_{40}$) was used as the active ingredient. Catalyst 7 having a content of heteropolyacid of 50% was obtained.

Catalyst 8

Diatomaceous earth having a SiO$_2$ content of 89%, a specific surface area of 2.8 m$^2$/g, a water absorbability of 50%, and a particle size within the range of 24 to 40 mesh was used as a carrier. According to the procedure described in connection with the preparation of catalyst 1, Catalyst 8 was prepared, which had a content of 10-molybdo-2-vanadophosphoric acid of 50%.

Catalyst 9

Silica gel having a specific surface area of 60 m$^2$/g, a water absorbability of 53%, and a particle size within the range of 24 to 40 mesh (manufactured and sold by Girdler Co. under the trade mark of 'T-869') was use as a carrier. According to the procedure described in the preparation of Catalyst 1, Catalyst 9 was prepared, which had a content of 10-molybdo-2-vanadophosphoric acid of 50%.

Catalyst 10

Zeolite (manufactured and sold by Union Showa K.K. under the trade mark of 'SK-40'; composition : SiO$_2$ 65.5%, Al$_2$O$_3$ 22.3%, Na$_2$O 12.2%) was formed into a suitable pellet and then calcined at 400° C. The calcined product was pulverized and then sieved to obtain a 24–40 mesh fraction. The resulting zeolite particles which had a specific surface area of 345.9 m$^2$/g and a water absorbability of 95% were used as a carrier. According to the procedure described in the preparation of Catalyst 1, Catalyst 10 was prepared, which had a content of 10-molybdo-2-vanadophosphoric acid of 50%.

Catalysts 11 and 12

Gamma-alumina having a specific surface area of 148 m$^2$/g, a water absorbability of 38%, and a particle size within the range of 24 to 40 mesh was used as a carrier. According to the procedure described in the preparation of catalyst 1, Catalysts 11 and 12 were prepared, which had contents of 10-molybdo-2-vanadophosphoric acid of 50% and 20%, respectively.

Catalyst 13

Gamma-alumina having a water absorption of 97.8% and a particle size within the range of 24 to 40 mesh (manufactured and sold by Shokubai Kasei Kogyo K.K. under the trade mark of "Active Alumina") was used as a carrier. According to the procedure described in the preparation of Catalyst 1, Catalyst 13 was prepared, which had a content of 10-molybdo-2-vanadophosphoric acid of 50%.

Catalyst 14

Alpha-alumina was used as a carrier. According to the procedure described in the preparation of Catalyst 1, Catalyst 14 was prepared, which had a content of 10-molybdo-2-vanadophosphoric acid of 50%. It was found that part of the carried ingredient powdered and separated from the carrier after drying.

Catalysts 15 and 16

Titania having a specific surface area of 70 m$^2$/g, a water absorbability of 45.8%, and a particle size within the range of 24 to 40 mesh used as a carrier. According to the procedure described in the preparation of Catalyst 1, Catalysts 15 and 16 were prepared, which had contents of 10-molybdo-2-vanadophosphoric acid of 50% and 20%, respectively.

Catalyst 17

Graphite having a water absorbability of less than 5% was used as a carrier. According to the procedure described in the preparation of Catalyst 1, Catalyst 17 was prepared, which had a content of 10-molybdo-2-vanadophosphoric acid of 50%. It was found that a major part of the carried ingredient separated from the carrier after drying.

Catalyst 18

Silicon carbide was used as a carrier. According to the procedure described in the preparation of Catalyst 1, Catalyst 18 was prepared, which had a content of 10-molybdo-2-vanadophosphoric acid of 50%. It was found that part of the carried ingredient powdered and separated from the carrier after drying.

Catalyst 19

Pumice powder having a water absorbability of less than 20% and a $SiO_2$ content of about 58% was used as a carrier. According to the procedure described in the preparation of Catalyst 1, Catalyst 19 was prepared, which had a content of 10-molybdo-2-vanadophosphoric acid of 50%. It was found that part of the carried ingredient powdered and separated from the carrier after drying.

B. CARRIED STATE OF CATALYSTS

The oxidative dehydrogenation of isobutyric acid was continuously carried out in the presence of each of the above-prepared catalysts. Reaction conditions were as follows.

Composition of the gas charge (volume ratio); isobutyric acid : steam : oxygen : nitrogen = 5 : 10 : 8.5 : 76.5

Contact time; 1.8 sec (SV = 2,000 hr$^{-1}$)

Reaction temperature; 320° C

Carried states of each catalyst before the reaction (i.e., immediately after the preparation) and after 1 hour of the reaction are shown in Table 1.

As obvious data in Table 1, the separation of active ingredients from carriers occurred with Catalysts 8, 9, 11, 14, 15, and 17-19. These catalysts cannot be continuously used.

C. REACTION

Example 1

The oxidative dehydrogenation of isobutyric acid was carried out in the presence of Catalyst 1 (with content of heteropolyacid of 50%). Reaction conditions were as follows.

Composition of the gas charge (volume ratio); isobutyric acid : steam : oxygen : nitrogen = 5 : 10 : 8.5 : 76.5

Contact time; 1.8 sec (SV = 2,000 hr$^{-1}$)

Reaction temperature; 320° C

Upon continued reaction for a period of 16 hours, the conversion rate of isobutyric acid and the selectivity to methacrylic acid were 99.0 and 70.2%, respectively. Upon further continued reaction for a total period of 32 hours, the conversion rate and the selectivity were 98.2 and 70.7%, respectively.

Comparative Examples 1 and 2

Using Catalysts 10 and 13 (both with contents of heteropolyacid of 50%), the oxidative dehydrogenation of isobutyric acid was carried out under the same conditions as in Example 1. The results are shown in Table 2.

Table 2

| Run | Catalyst No. | Conversion rate of isobutyric acid | Selectivity to methacrylic acid |
|---|---|---|---|
| Example 1 | 1 | 99.0 % | 70.2 % |
| Comparative Example 1 | 10 | 74.0 % | 64.0 % |
| Comparative Example 2 | 13 | 92.0 % | 25.9 % |

Example 2

The oxidative dehydrogenation of isobutyric acid was carried out in the presence of Catalyst 7 (with Table 1

| Catalyst | Kind | Carrier $SiO_2$ content (%) | Water absorbability (%) | Content of heteropolyacid (%) | Carried state of catalysts Before reaction | After reaction |
|---|---|---|---|---|---|---|
| 1 | diatomaceous earth | 89 | 100 | 50 | good | good |
| 2 | diatomaceous earth | 89 | 100 | 20 | good | good |
| 3 | diatomaceous earth | 89 | 90 | 50 | good | good |
| 4 | diatomaceous earth | 89 | 90 | 20 | good | good |
| 5 | silica gel | 100 | 100 | 50 | good | good |
| 6 | silica gel | 100 | 100 | 20 | good | good |
| 7 | diatomaceous earth | 89 | 100 | 50 | good | good |
| 8 | diatomaceous earth | 89 | 50 | 50 | slightly separated | partly powdered and separated |
| 9 | silica gel | 100 | 53 | 50 | partly separated | partly separated |
| 10 | zeolite | 66 | 95 | 50 | good | good |
| 11 | γ-alumina | — | 38 | 50 | partly separated | partly powdered and separated |
| 12 | γ-alumina | — | 38 | 20 | good | good |
| 13 | γ-alumina | — | 97.8 | 50 | good | good |
| 14 | α-alumina | — | <20 | 50 | partly powdered and separated | — |
| 15 | titania | — | 45.8 | 50 | partly separated | partly powdered and separated |
| 16 | titania | — | 45.8 | 20 | good | good |
| 17 | grahite | — | <5 | 50 | mostly separated | — |
| 18 | silicon carbide | — | — | 50 | partly powdered and separated | — |
| 19 | pumice powder | 58 | <20 | 50 | partly powdered and separated | — | content of heteropolyacid of 50%). Reaction conditions were as follows.

Composition of the gas charge (volume ratio); isobutyric acid : oxygen : nitrogen = 2.8 : 2.8 : 94.4
Contact time; 4.5 sec
Reaction temperature; 282° C The conversion rate of isobutyric acid was 87.9% and the selectivity of methacrylic acid was 65.7%.

Examples 3-5 and Comparative Examples 3-4

The oxidative dehydrogenation of isobutyric acid was carried out in the presence of each of Catalysts 2, 4, 6, 12, and 16 (each with content of heteropolyacid of 20%). Reaction conditions were as follows.

Composition of the gas charge (volume ratio); isobutyric acid : steam : oxygen : nitrogen = 5 : 10 : 8.5 : 76.5
Contact time; 0.6 sec (SV = 6,000 hr$^{-1}$)
Reaction temperature; 285° C The results are shown in Table 3.

Table 3

| Run | Catalyst No. | Conversion rate of isobutyric acid | Selectivity to methacrylic acid |
|---|---|---|---|
| Example 3 | 2 | 56.0 % | 70.0 % |
| Example 4 | 4 | 54.0 % | 70.0 % |
| Example 5 | 6 | 60.2 % | 65.0 % |
| Comparative Example 3 | 12 | 14.7 % | 31.7 % |
| Comparative Example 4 | 16 | 62.0 % | 14.7 % |

What is claimed is:

1. In a process for the manufacture of methacrylic acid which comprises reacting oxygen and isobutyric acid in vapor phase in the presence of a supported catalyst containing a heteropolyacid having the general formula:

$$H_{3+x}Mo_{12-x-y}W_yV_xPO_{40}$$

wherein $x$ and $y$ are independently 0, 1, 2 or 3 and $x + y < 5$, and/or a reduced form of said heteropolyacid, the improvement wherein the carrier for said catalyst has a $SiO_2$ content of at least 70% and a water absorbability of at least 60%.

2. The process according to claim 1, wherein said carrier is silica gel having a water absorbability of at least 60%.

3. The process according to claim 1, wherein said carrier is diatomaceous earth having a water absorbability of at least 60%.

4. The process of claim 1 wherein the molar ratio of oxygen to isobutyric acid is 0.1 to 10.

5. The process of claim 1 wherein the reaction temperature is 200 to 450° C.

6. The process of claim 1 wherein the reaction pressure is 0.5 to 30 kg/cm$^2$.

* * * * *